United States Patent
Chen et al.

(10) Patent No.: US 9,953,208 B2
(45) Date of Patent: Apr. 24, 2018

(54) APPARATUS FOR DETECTING CELLS BEING INFECTED WITH HUMAN PAPILLOMAVIRUS (HPV) AND A DETECTION METHOD THEREFOR

(71) Applicant: Metal Industries Research & Development Centre, Kaohsiung (TW)

(72) Inventors: Yen-Chun Chen, Kaohsiung (TW); Ming-Hui Cheng, Kaohsiung (TW); Yu-Fen Kuo, Kaohsiung (TW); Po-Wei Pan, Kaohsiung (TW); Tsung-Chih Yu, Kaohsiung (TW)

(73) Assignee: METAL INDUSTRIES RESEARCH & DEVELOPMENT CENTRE, Kaohsiung (TW)

( * ) Notice: Subject to any disclaimer, the term of this patent is extended or adjusted under 35 U.S.C. 154(b) by 35 days.

(21) Appl. No.: 15/081,987

(22) Filed: Mar. 28, 2016

(65) Prior Publication Data

US 2017/0169283 A1    Jun. 15, 2017

(30) Foreign Application Priority Data

Dec. 9, 2015    (TW) .............................. 104141378 A (51) Int. Cl.
*G06K 9/00* (2006.01)
*G01N 33/483* (2006.01)
(Continued)

(52) U.S. Cl.
CPC ....... *G06K 9/00147* (2013.01); *G01N 33/483* (2013.01); *G06T 7/0085* (2013.01);
(Continued)

(58) Field of Classification Search
None
See application file for complete search history.

(56) References Cited

U.S. PATENT DOCUMENTS 5,784,162 A * 7/1998 Cabib .................. C12Q 1/6841
250/461.2
8,687,864 B2 * 4/2014 Matsumoto ........... G06T 7/0012
382/128

(Continued)

FOREIGN PATENT DOCUMENTS

TW          201510936 A       3/2015

OTHER PUBLICATIONS

Ko, Chien-Chuan. Prognostic analysis and automatic diagnosis of Breast Carcinoma by using Digital Image Processing. Jul. 2009. Department of Computer Science and Information Engineering National Chiayi University Master Thesis.

(Continued)

*Primary Examiner* — Avinash Yentrapati
(74) *Attorney, Agent, or Firm* — Volpe and Koenig, P.C.

(57) ABSTRACT

The present invention discloses a method for detecting whether cells are infected with human papillomavirus (HPV), and the method includes: (a) capturing a contour of a cell of a cell image, wherein the contour has a contour pixel thereon; (b) identifying a tangent of the contour pixel on the contour to define in relation to the tangent a first side and a second side opposite to the first side, wherein the first side indicates the intracellular region of the cell and the second side indicates the extracellular region of the cell; (c) calculating an optical parameter average of the plurality of pixels on both of the first side and the second side; and (d) determining whether the cell is infected with HPV based on whether the optical parameter average on the first side is smaller than that on the second side.

20 Claims, 5 Drawing Sheets

(51) Int. Cl.
 G06T 7/00 (2017.01)
 G06T 7/40 (2017.01)
(52) U.S. Cl.
 CPC ........ G06T 7/408 (2013.01); *G01N 2333/025* (2013.01); *G06T 2207/10024* (2013.01); *G06T 2207/20084* (2013.01); *G06T 2207/30004* (2013.01)

(56) References Cited

U.S. PATENT DOCUMENTS

| | | | | |
|---|---|---|---|---|
| 2010/0080439 | A1* | 4/2010 | Karam | G06K 9/00134 382/133 |
| 2010/0172569 | A1* | 7/2010 | Takagi | G01N 15/1475 382/133 |
| 2012/0114219 | A1* | 5/2012 | Nakagawa | C12M 41/14 382/133 |
| 2015/0078640 | A1* | 3/2015 | Guo | G06T 7/0083 382/131 |

OTHER PUBLICATIONS

Office Action mailed in corresponding Taiwanese Patent Appln. No. 104141378 dated Aug. 12, 2015, consisting of 4 pp.

* cited by examiner

$$S_x = \begin{array}{|c|c|c|c|c|} \hline 1 & 2 & 0 & -2 & -1 \\ \hline 4 & 8 & 0 & -8 & -4 \\ \hline 6 & 12 & 0 & -12 & -6 \\ \hline 4 & 8 & 0 & -8 & -4 \\ \hline 1 & 2 & 0 & -2 & -1 \\ \hline \end{array} \quad S_y = \begin{array}{|c|c|c|c|c|} \hline -1 & -4 & -6 & -4 & -1 \\ \hline -2 & -8 & -12 & -8 & -2 \\ \hline 0 & 0 & 0 & 0 & 0 \\ \hline 2 & 8 & 12 & 8 & 2 \\ \hline 1 & 4 & 6 & 4 & 1 \\ \hline \end{array}$$

APPARATUS FOR DETECTING CELLS BEING INFECTED WITH HUMAN PAPILLOMAVIRUS (HPV) AND A DETECTION METHOD THEREFOR

CROSS-REFERENCE TO RELATED APPLICATION AND CLAIM OF PRIORITY

The application claims the benefit of Taiwan Patent Application No. 104141378, filed on Dec. 9, 2015, at the Taiwan Intellectual Property Office, the disclosures of which are incorporated herein in their entirety by reference.

FIELD OF THE INVENTION

The present invention is related to an apparatus and a method for detecting whether cells are infected with Human Papillomavirus (HPV), specifically for detecting whether cells are infected with HPV using innovative image analysis technology.

BACKGROUND OF THE INVENTION

Human Papillomavirus (HPV) is a DNA virus from the Papillomaviridae family and *Papillomavirus* genus, which mainly infects human epidermis and mucosa tissues. About 170 types of HPV been identified, wherein some types of HPV cause warts and cancer after invading the human body, but other HPVs do not cause any symptoms.

HPV can infect humans and animals, and mainly invades epidermis cells and the inner layers of tissues. According to the types of the infected tissues, HPV can be distinguished into epidermis types and mucosa types, wherein the epidermis types mainly induce an infection on the epidermis of the hands and feet, and the mucosa types cause the infection in the mouth, throat, respiratory tract and urogenital tract of patients. HPV causes the proliferation of skin keratinocytes and results in skin warts (such as flat warts, common warts or plantar warts) on the hands or feet. In general, these warts may disappear after 1 to 5—years of infection, but some infected skin may result in skin cancer, and some may result in oral squamous cell carcinoma.

There are 30-40 types of HSV which infect genitalia and the peripheral skin via sexual behavior, and some types of HSV may induce warts on the sexual organs. If a person is repeatedly infected with some types of HPV with high risk and do not induce obvious symptoms (e.g. warts and so on), the invasion of these HPV may develop into precancerous lesions, or even invasive cancer. An HPV infection is one of the key causes of cervical cancer, which is commonly caused by sexual behavior or by mother-to-child transmission. Some research indicates that 99.7% of cervical cancers are caused by HPV infection.

The common methods for detecting HSV-infected cells include a cytologic test and a thin-cytologic test in the early phase. These tests are the traditional manual identification methods, which have the problems of accuracy and timeliness. Recently, DNA detection methods, such as in situ hybridization, HPV DNA direct detection, amplification hybridization, HPV mRNA detection and microarray, have been developed because of breakthroughs in DNA techniques. At present, although molecular diagnostic technology is predominantly used to detect HPV, it is typically paid for the patient's own expense and the cost is high. Although the U.S. Food and Drug Administration (FDA) approved Roche's Cobas® HPV Test (Roche Molecular systems Inc.) as a first-line primary screening tool in April 2014, there is no officially suggested first-line primary screening tool for any age group accepted by many medical associations (e.g. the American Association for Cancer Research (AACR)). In addition, although the Australian authority approved the Cobas® HPV Test as a first-line primary screening tool in some administrative areas in 2015, the Cobas® HPV Test is not highly recommended. Accordingly, the scientific community still uses HPV detection methods such as the image cytologic test which is manually determined. However, there are still problems that cells infected with HPV cannot be quickly and accurately determined.

Furthermore, Pap smears (also called the Papanicolaou test) are determined one by one by pathologists to identify and classify the characteristics of the Pap smears. However, the number of Pap smears has expanded far faster than the number of pathologists. This causes an excessive workload for the pathologists and could affect the accuracy of the identification of Pap smears. Therefore, there is a gear need for digital pathologic screening and diagnostic equipment to identify the HPV-infected cells (such as from the Pap smears) using digital diagnostic screening and diagnosis, to help pathologists identify and classify the characteristics, so that the screening time for the Pap smears can be reduced, while also maintaining the accuracy and reliability.

To sum up the above disadvantages, it is ideal to have new digital pathologic screening and diagnostic equipment and a method to overcome the above-mentioned defects. It is therefore the Applicant's attempt to deal with the many limitations in the prior art.

SUMMARY OF THE INVENTION

To determine whether a cell is infected with HPV more rapidly, accurately and reliably, the present invention discloses digital pathologic screening and diagnostic equipment to directly determine whether the cell is infected with HPV to shorten the screening time of the Pap smears and maintain the accuracy and reliability of the test.

In accordance with one aspect of the present disclosure, an image analyzing device to detect whether a cell having a cell image is infected with Human Papillomavirus (HPV) is disclosed. The image analyzing device includes: a color transformation unit configured to transform a red, green and blue (RGB) color coordinate of each pixel in the cell image into a hue, saturation and value (HSV) color coordinate, wherein the cell image is transformed into an HSV image; a cell outline capture unit configured to capture a cell outline of the cell from the HSV image; an outline pixel capture unit configured to sample at least one outline pixel on the cell outline; an identification unit configured to identify a tangent of each of the at least one outline pixel on the cell outline, and define a first side and a second side opposite to the first side in relation to the tangent, wherein the first side indicates an extracellular region of the cell and the second side indicates an intracellular region of the cell; a calculation unit configured to calculate one of a brightness average and a hue average of a plurality of pixels respectively on the first side and the second side; and a determination unit configured to determine that the cell is infected with HPV when one of two states that the brightness average of the first side is smaller than that of the second side and the hue average of the first side is greater than that of the second side is true, and determine that the cell is not infected with HPV when one of the two states that the brightness average of the first side is no less than that of the second side and the hue average of the first side is no greater than that of the second side is true.

In accordance with another aspect of the present disclosure, a method implemented by an image analyzing device for detecting whether a cell having a cell image is infected with a virus is disclosed. The method includes steps of: (a) using the image analyzing device to capture a cell outline on the cell image and sample outline pixels on the cell outline; (b) using the image analyzing device to identify respective tangents of the outline pixels and define a first side and a second side opposite to the first side in relation to each of the tangents, wherein the first side indicates an extracellular region of the cell, and the second side indicates an intracellular region of the cell; (c) using the image analyzing device to calculate one of a brightness average and a hue average of pixels respectively on the first side and the second side; and (d) using the image analyzing device to determine that the cell is infected with the virus when one of the two states that the brightness average of the first side is smaller than that of the second side and the hue average of the first side is greater than that of the second side is true, and determine that the cell is not infected with the virus when one of the two states that the brightness average of the first side is no less than that of the second side and the hue average of the first side is no greater than that of the second side is true.

In accordance with one more aspect of the present disclosure, a method implemented by an image analyzing device for detecting whether a cell having a cell image is infected with a virus is disclosed. The method includes steps of: (a) using the image analyzing device to capture a cell outline from the cell image, wherein the cell outline includes an outline pixel; (b) using the image analyzing device to identify a tangent of the outline pixel and define in relation to the tangent a first side and a second side opposite to the first side, wherein the first side indicates an extracellular region of the cell, and the second side indicates an intracellular region of the cell; (c) using the image analyzing device to calculate an optical parameter average of a plurality of pixels on either of the first side and the second side; and (d) using the image analyzing device to determine whether the cell is infected with the virus based on whether the optical parameter average on the first side is smaller than that on the second side.

Other objectives, advantages and efficacies of the present invention will be described in detail below taken from the preferred embodiments with reference to the accompanying drawings.

DETAILED DESCRIPTION OF THE PREFERRED EMBODIMENTS

The present invention will now be described more specifically with reference to the following Embodiments. It is to be noted that the following descriptions of the preferred Embodiments of this invention are presented herein for the purpose of illustration and description only; they are not intended to be exhaustive or to be limited to the precise form disclosed. In the preferred embodiments, the same reference numeral represents the same element in each embodiment.

In one embodiment, the present invention discloses a device and a method for detecting whether a cell is infected with HPV. The present invention uses a detection system to capture the variation characteristics of the cell, calculate a brightness average or a hue average of intracellular pixels and extracellular pixels and determine whether the cell is infected with HPV according to the brightness average or the hue average from the two sides of the cell.

Figure 1:
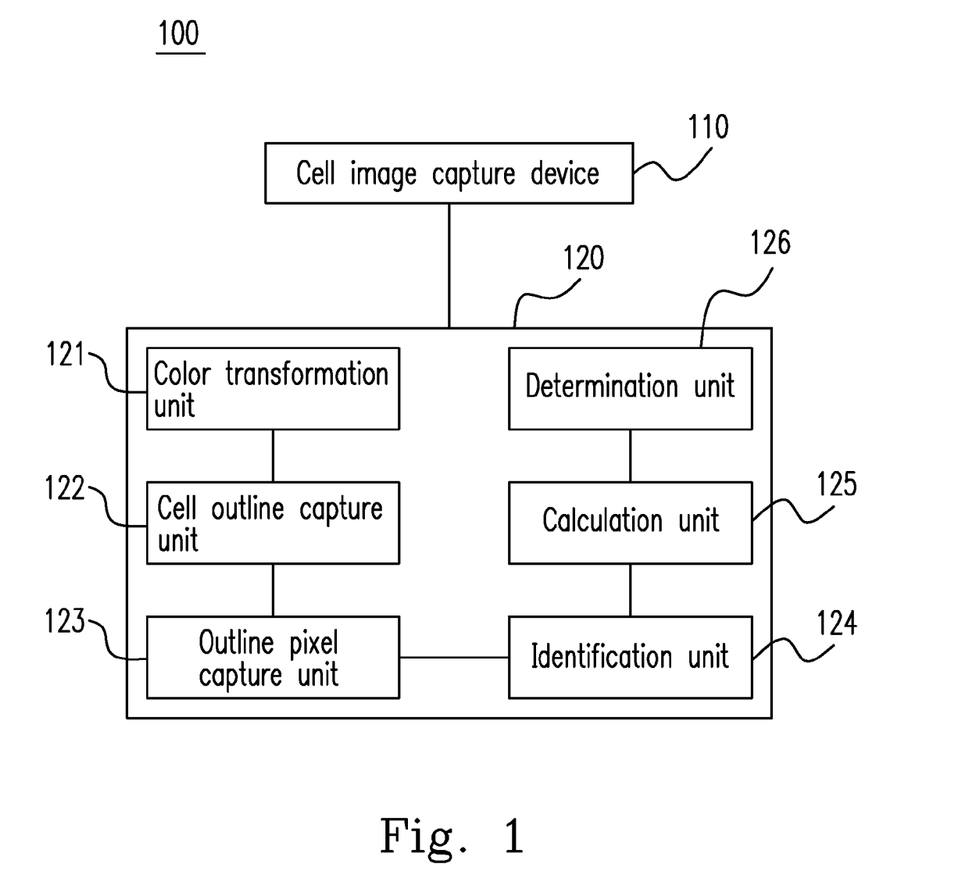
FIG. 1 is a schematic diagram of a system of the present invention to detect whether a cell is infected with HPV.
Figure 2:
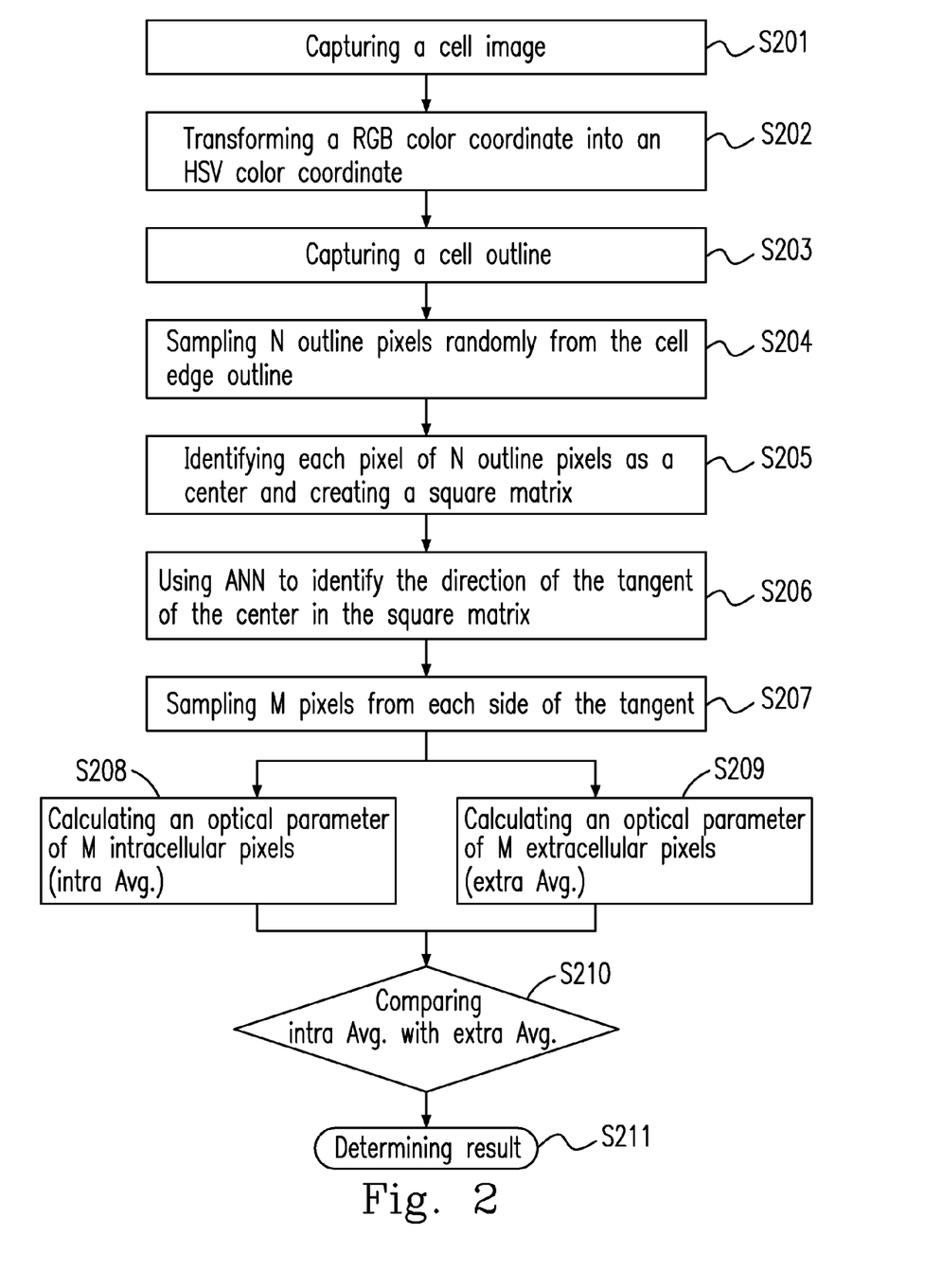
FIG. 2 is a schematic diagram of a method of the present invention for detecting whether a cell is infected with HPV.

Please refer to FIGS. 1 and 2, which respectively are schematic diagrams of a system and a method of the present invention to detect whether a cell is infected with HPV. The detection system 100 includes a cell image capture device 110 and an image analyzing device 120, wherein the image analyzing device 120 includes a color transformation unit 121, a cell outline capture unit 122, an outline pixel capture unit 123, an identification unit 124, a calculation unit 125 and a determination unit 126.

The cell image capture device 110 captures a treated cell sample (Step 201 in FIG. 2), and the cell sample image is a single cell. In one embodiment, the cell sample may be a Pap smear or another cell sample taken from epidermis cells or mucosa cells of a human being. The cell image capture device 110 may be a photomicrographic device. The cell sample may be taken by common or regular methods when it is sampled, and then the treated cell sample is captured using photomicrography to obtain a single cell image.

The color transformation unit 121 transforms a red, green and blue (RGB) color coordinate of each pixel on the single cell image into a hue, saturation and value (HSV) color coordinate (Step 202 in FIG. 2) to obtain an HSV image, and reserves the hue value or the brightness value of each pixel.

Figure 3:
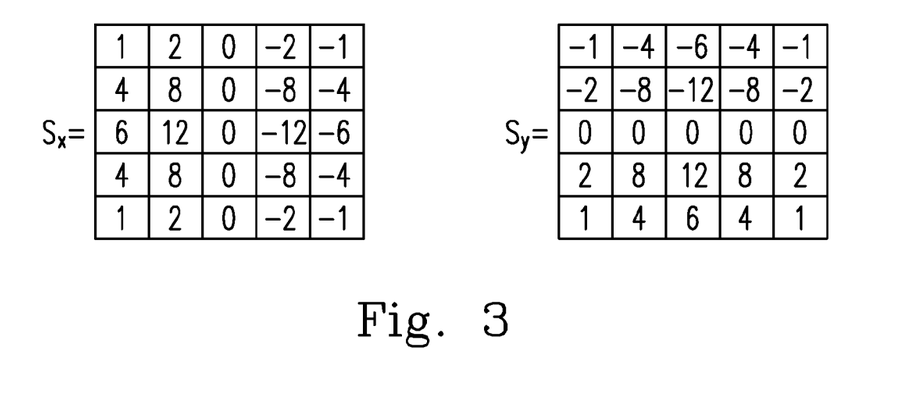
FIG. 3 is a schematic diagram showing two 5×5 kernels in a Sobel operator.

After obtaining the HSV image, the cell outline capture unit 122 uses a Sobel operator to detect the edge of the cell, and captures the cell outline using a thinning algorithm (Step 203 in FIG. 2), wherein the cell outline is the cell edge outline. In one embodiment, two 5*5 kernels in the Sobel operator (for X axis and Y axis as shown in FIG. 3) are used to detect the edge of the cell.

The outline pixel capture unit 123 samples N outline pixels randomly from the captured cell edge outline (Step 204 in FIG. 2). In one embodiment, N is 1-100, and N preferably is 10-100. Larger N values increase the accuracy of the test. In another embodiment, as shown in FIG. 5, the outline pixel capture unit 123 samples 20 outline pixels 502 from the cell edge outline 504, and each of the outline pixels 502 is spaced near each other on the cell edge outline 504.

Figure 4:
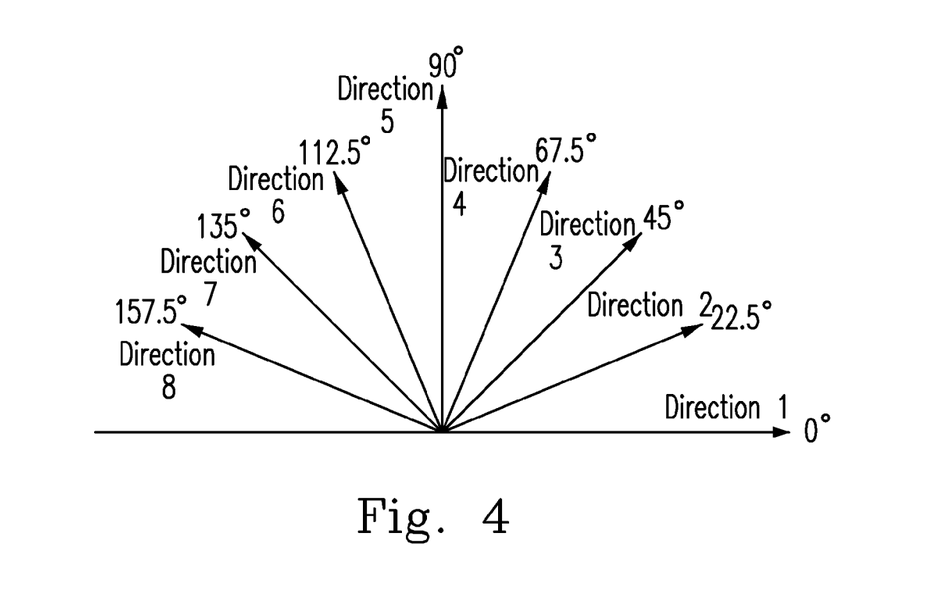
FIG. 4 is a schematic diagram showing 8 directions identified by an artificial neural network (ANN).

The identification unit 124 identifies each pixel of the N outline pixels as a center and creates a square matrix (Step 205 in FIG. 2). In one embodiment, the square matrix is no less than a 5×5 matrix. Preferably, the square matrix is a 7×7 matrix. The identification unit 124 uses an artificial neural network (ANN) to identify the direction of the center (i.e. a tangent direction of the center in the square matrix on the cell edge outline) (Step 206 in FIG. 2). The ANN obtains a training parameter based on previous training of various types of cell edge images. Using the 7×7 matrix as an example, 49 pixels in the 7×7 matrix are used as input values in each training, and the direction value of the center in the predefined 7×7 matrix is an output value of ANN. After calculating the input values of 49 pixels in the matrix using the ANN, one of 8 directions (i.e. 0°, 22.5°, 45°, 67.5°, 90°, 112.5°, 135° and 157.5°) is output (as shown in FIG. 4). In one embodiment, as shown in FIG. 5, a 7×7 matrix 503 is created based on the outline pixel 502 on the cell image 501, and the direction of the tangent 505 on the outline pixel 502 on the cell edge outline 504 is 135° (direction 7) after the ANN identification.

Figure 5:
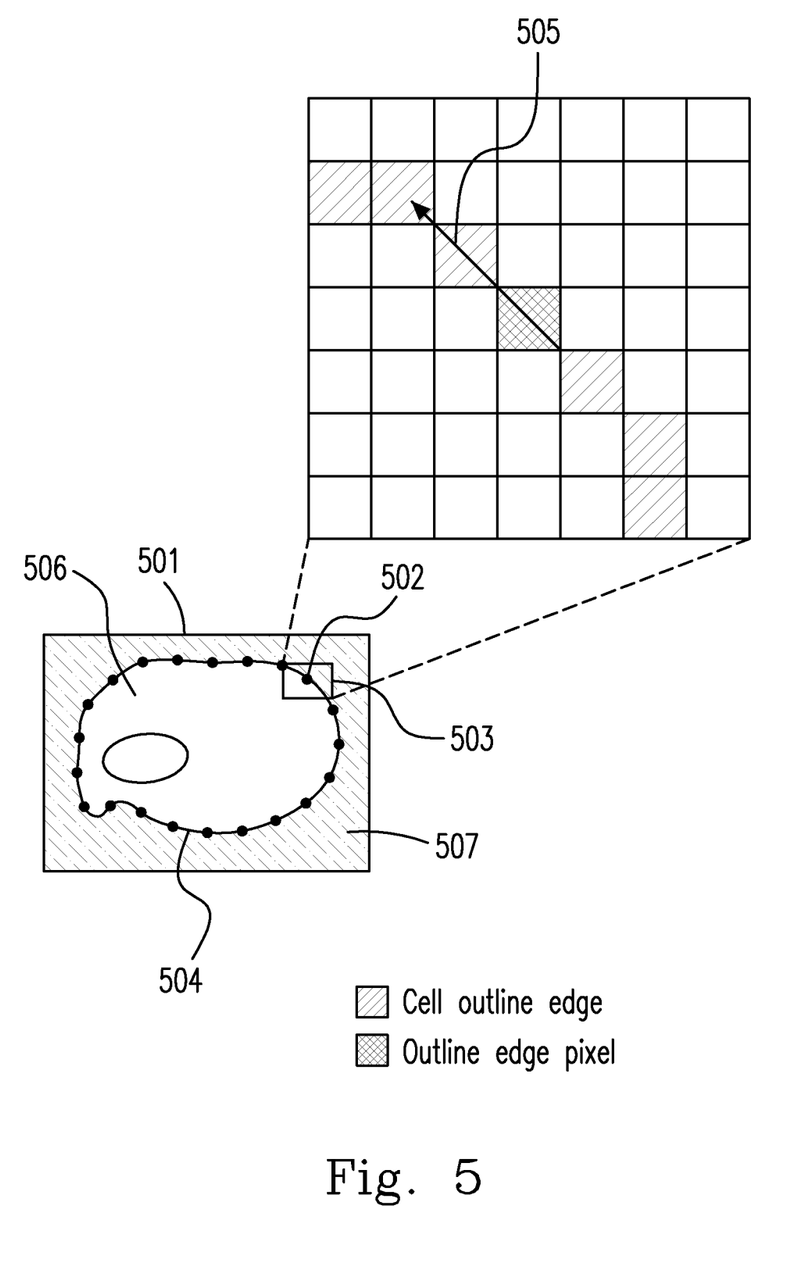
FIG. 5 is a schematic diagram of identifying a tangent of a cell outline pixel on a cell edge outline using the ANN.
Figure 6:
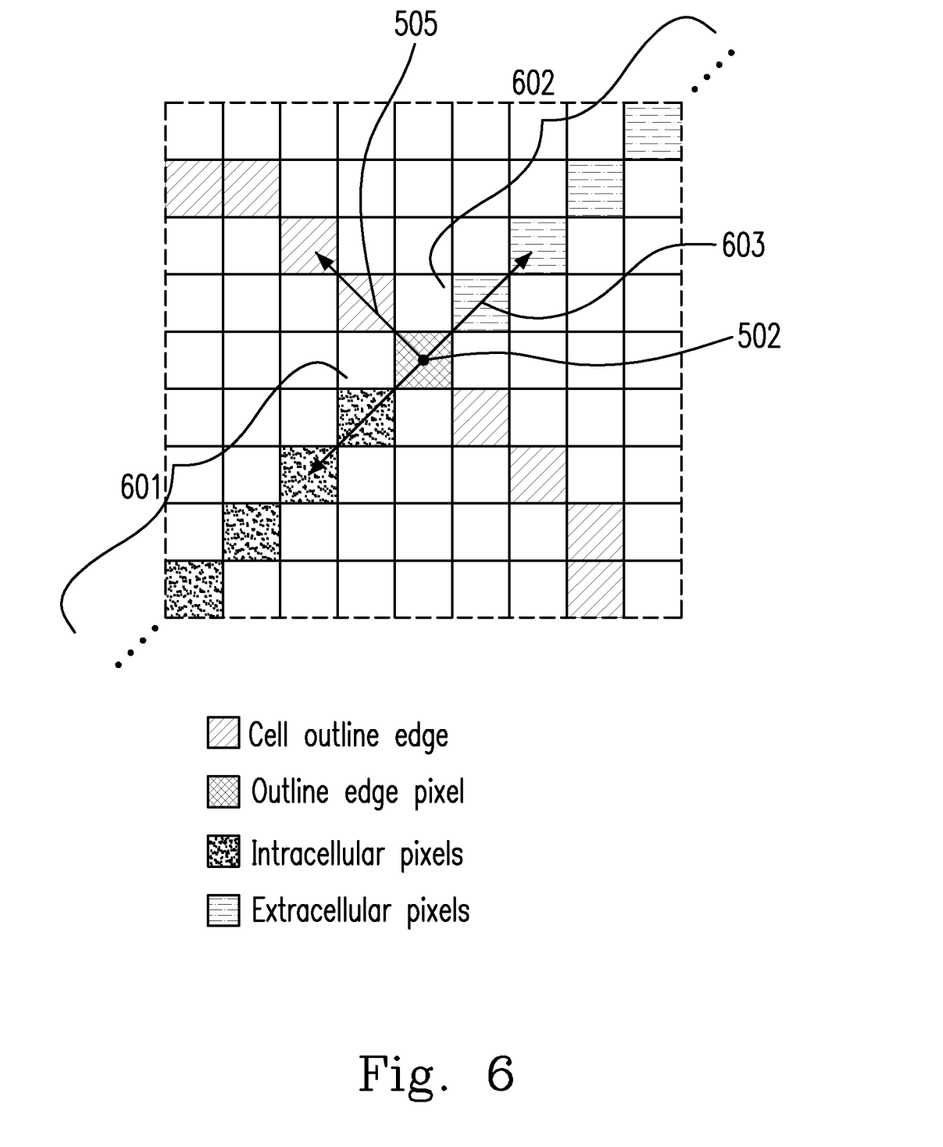
FIG. 6 is a schematic diagram of calculating a brightness average or a hue average of pixels on the two sides of the tangent.

After identifying the direction of the tangent 505 on the outline pixel 502 on the cell edge outline 504, the identification unit 124 identifies that an intracellular region 506 is on the left or right side of the tangent 505, or an extracellular region 507 is on the left or right side of the tangent 505, and samples M pixels from each side of the tangent 505 (as shown in FIG. 5 and referring to Step 207 in FIG. 2). In one embodiment, as shown in FIG. 6, the identification unit 124 samples M intracellular pixels 601 and M extracellular pixels 602 on a line 603 respectively from the intracellular region 506 and from the extracellular region 507, wherein the line 603 is perpendicular to the tangent 505 and passes through the outline edge pixel 502. The total number of M is sampled based on the resolution of the cell capturing device 100, and M is a positive integer. Preferably, M is 1000-3000, and can be defined by a user.

The calculation unit 125 calculates an optical parameter average of M intracellular pixels (Step 208 in FIG. 2) and an optical parameter average of M extracellular pixels (Step 209 in FIG. 2), wherein the optical parameter average includes a hue average and a brightness average.

The determination unit 126 determines whether the cell is infected with HPV (Step 211 in FIG. 2) by comparing at least one of the hue average and the brightness average of the intracellular pixels with those of the extracellular pixels (Step 210 in FIG. 2). If one of two states that the brightness average of the first side is smaller than that of the second side and the hue average of the first side is greater than that of the second side is true, the determination unit 126 determines the cell is infected with HPV, and if one of the two states that the brightness average of the first side is no less than that of the second side and the hue average of the first side is no greater than that of the second side is true, the determination unit 126 determines the cell is not infected with HPV. In one embodiment, when the brightness average of the extracellular pixels is smaller than that of the intracellular pixels (or the hue average of the extracellular pixels is greater than that of the intracellular pixels), it is determined that the cell is infected with HPV. In one embodiment, when the brightness average of extracellular pixels is larger than or equal to that of the intracellular pixels (or the hue average of the extracellular pixels is smaller than or equal to that of the intracellular pixels), it is determined that the cell is not infected with HPV.

Although the present invention has been described with reference to certain exemplary embodiments thereof, it can be understood by those skilled in the art that a variety of modifications and variations may be made to the present invention without departing from the spirit or scope of the present invention defined in the appended claims, and their equivalents.

Embodiments

1. An image analyzing device to detect whether a cell having a cell image is infected with Human Papillomavirus (HPV), including: a color transformation unit configured to transform a red, green and blue (RGB) color coordinate of each pixel in the cell image into a hue, saturation and value (HSV) color coordinate, wherein the cell image is transformed into an HSV image; a cell outline capture unit configured to capture a cell outline of the cell from the HSV image; an outline pixel capture unit configured to sample at least one outline pixel on the cell outline; an identification unit configured to identify a tangent of each of the at least one outline pixel on the cell outline, and define a first side and a second side opposite to the first side in relation to the tangent, wherein the first side indicates an extracellular region of the cell and the second side indicates an intracellular region of the cell; a calculation unit configured to calculate one of a brightness average and a hue average of a plurality of pixels respectively on the first side and the second side; and a determination unit configured to determine that the cell is infected with HPV when one of two states that the brightness average of the first side is smaller than that of the second side and the hue average of the first side is greater than that of the second side is true, and determine that the cell is not infected with HPV when one of the two states that the brightness average of the first side is no less than that of the second side and the hue average of the first side is no greater than that of the second side is true.

2. The image analyzing device according to Embodiment 1, wherein the cell image is an image of a single cell.

3. The image analyzing device according to Embodiment 1 or 2, wherein the cell is one of an epidermis cell and a mucosa cell taken from a human being.

4. The image analyzing device according to any one of Embodiments 1 to 3, wherein the cell outline capture unit is configured to detect the cell in the cell image using a Sobel operator, and capture the cell outline using a thinning algorithm.

5. The image analyzing device according to any one of Embodiments 1 to 4, wherein the calculation unit is configured to calculate one of the brightness average and the hue average of the plurality of pixels along a line, wherein the line is perpendicular to the tangent and passes through a corresponding one of the at least one outline pixel.

6. A method implemented by an image analyzing device for detecting whether a cell having a cell image is infected with a virus, including: (a) using the image analyzing device to capture a cell outline on the cell image and sample outline pixels on the cell outline; (b) using the image analyzing device to identify respective tangents of the outline pixels and define a first side and a second side opposite to the first side in relation to each of the tangents, wherein the first side indicates an extracellular region of the cell, and the second side indicates an intracellular region of the cell; (c) using the image analyzing device to calculate one of a brightness average and a hue average of pixels respectively on the first side and the second side; and (d) using the image analyzing device to determine that the cell is infected with the virus when one of the two states that the brightness average of the first side is smaller than that of the second side and the hue average of the first side is greater than that of the second side is true, and determine that the cell is not infected with the virus when one of the two states that the brightness average of the first side is no less than that of the second side and the hue average of the first side is no greater than that of the second side is true.

7. The method according to Embodiment 6, wherein the virus is Human Papillomavirus (HPV).

8. The method according to Embodiment 6 or 7, wherein the cell is one of an epidermis cell and a mucosa cell taken from a human being.

9. The method according to any one of Embodiments 6 to 8, wherein the image analyzing device samples 2-100 outline pixels.

10. The method according to any one of Embodiments 6 to 9, wherein the cell image is captured using a photomicrography.

11. The method according to any one of Embodiments 6 to 10, wherein a total number of the pixels being sampled is defined by a user and is a positive integer.

12. The method according to any one of Embodiments 6 to 11, wherein a red, green and blue (RGB) color coordinate of each pixel in the cell image is transformed into a hue, saturation, value (HSV) color coordinate so as to transform an RGB image with the cell outline into an HSV image with the cell outline.

13. The method according to any one of Embodiments 6 to 12, further including: (a1) using a Sobel operator included in the image analyzing device to detect the cell outline of the cell image; and (a2) using a thinning algorithm included in the image analyzing device to capture the cell outline.

14. The method according to any one of Embodiments 6 to 13, wherein the Sobel operator uses two 5×5 kernels to detect the cell outline of the cell image.

15. The method according to any one of Embodiments 6 to 14, wherein the outline pixels are spaced on the cell outline.

16. The method according to any one of Embodiment 6 to 15, wherein the tangents are identified using an artificial neural network (ANN) included in the image analyzing device.

17. The method according to any one of Embodiments 6 to 16, wherein the image analyzing device calculates one of the brightness average and the hue average of the pixels on plural lines, wherein each of the lines is perpendicular to a specific one of the tangents and passes through a specific one of the outline pixels.

18. A method implemented by an image analyzing device for detecting whether a cell having a cell image is infected with a virus, including: (a) using the image analyzing device to capture a cell outline from the cell image, wherein the cell outline includes an outline pixel; (b) using the image analyzing device to identify a tangent of the outline pixel and define in relation to the tangent a first side and a second side opposite to the first side, wherein the first side indicates an extracellular region of the cell, and the second side indicates an intracellular region of the cell; (c) using the image analyzing device to calculate an optical parameter average of a plurality of pixels on both of the first side and the second side; and (d) using the image analyzing device to determine whether the cell is infected with the virus based on whether the optical parameter average on the first side is smaller than that on the second side.

19. The method according to Embodiment 18, wherein the optical parameter average includes at least one of a brightness average and a hue average.

20. The method according to Embodiment 18 or 19, wherein the image analyzing device determines that the cell is infected with the virus when one of two states that the brightness average of the first side is smaller than that of the second side and the hue average of the first side is greater than that of the second side is true, and determines that the cell is not infected with the virus when one of the two states that the brightness average of the first side is greater than that of the second side and the hue average of the first side is smaller than that of the second side is true.

What is claimed is:

1. An image analyzing device to detect whether a cell having a cell image is infected with Human Papillomavirus (HPV), comprising:

a color transformation unit connected to an input of the image analyzing device and configured to transform a red, green and blue (RGB) color coordinate of each pixel in the cell image into a hue, saturation and value (HSV) color coordinate, wherein the cell image is transformed into an HSV image;

a cell outline capture unit connected to the color transformation unit and configured to capture a cell outline of the cell from the HSV image;

an outline pixel capture unit connected to the cell outline capture unit and configured to sample at least one outline pixel on the cell outline;

an identification unit connected to the outline pixel capture unit and configured to identify a tangent of each of the at least one outline pixel on the cell outline, and define a first side and a second side opposite to the first side in relation to the tangent, wherein the first side indicates an extracellular region of the cell and the second side indicates an intracellular region of the cell;

a calculation unit connected to the identification unit and configured to calculate one of a brightness average and a hue average of a plurality of pixels respectively on the first side and the second side; and a determination unit connected to the calculation unit and configured to determine that the cell is infected with HPV when one of two states that the brightness average of the first side is smaller than that of the second side and the hue average of the first side is greater than that of the second side is true, and determine that the cell is not infected with HPV when one of the two states that the brightness average of the first side is no less than that of the second side and the hue average of the first side is no greater than that of the second side is true.

2. The image analyzing device as claimed in claim 1, wherein the outline pixel capture unit is configured to sample one outline pixel on the cell outline and the cell image is an image of a single cell.

3. The image analyzing device as claimed in claim 1, wherein the outline pixel capture unit is configured to sample one outline pixel on the cell outline and the cell is one of an epidermis cell and a mucosa cell taken from a human being.

4. The image analyzing device as claimed in claim 1, wherein the cell outline capture unit is configured to detect the cell in the cell image using a Sobel operator, and capture the cell outline using a thinning algorithm.

5. The image analyzing device as claimed in claim 1, wherein the calculation unit is configured to calculate one of the brightness average and the hue average of the plurality of pixels along a line, wherein the line is perpendicular to the tangent and passes through a corresponding one of the at least one outline pixel.

6. A method implemented by an image analyzing device for detecting whether a cell having a cell image is infected with a virus, comprising: (a) using the image analyzing device to capture a cell outline on the cell image and sample outline pixels on the cell outline; (b) using the image analyzing device to identify respective tangents of the outline pixels and define a first side and a second side opposite to the first side in relation to each of the tangents, wherein the first side indicates an extracellular region of the cell, and the second side indicates an intracellular region of the cell; (c) using the image analyzing device to calculate one of a brightness average and a hue average of pixels on the first side and the second side; and (d) using the image analyzing device to determine that the cell is infected with the virus when one of the two states that the brightness average of the first side is smaller than that of the second side and the hue average of the first side is greater than that of the second side is true, and determine that the cell is not infected with the virus when one of the two states that the brightness average of the first side is no less than that of the second side and the hue average of the first side is no greater than that of the second side is true.

7. The method as claimed in claim 6, wherein the virus is Human Papillomavirus (HPV).

8. The method as claimed in claim 6, wherein the cell is one of an epidermis cell and a mucosa cell taken from a human being.

9. The method as claimed in claim 6, wherein the image analyzing device samples 2-100 outline pixels.

10. The method as claimed in claim 6, wherein the cell image is captured using a photomicrography.

11. The method as claimed in claim 6, wherein a total number of the pixels being sampled is defined by a user and is a positive integer.

12. The method as claimed in claim 6, wherein a red, green and blue (RGB) color coordinate of each pixel in the cell image is transformed into a hue, saturation, value (HSV) color coordinate so as to transform an RGB image with the cell outline into an HSV image with the cell outline.

13. The method as claimed in claim 12, further comprising: (a1) using a Sobel operator included in the image analyzing device to detect the cell outline of the cell image; and (a2) using a thinning algorithm included in the image analyzing device to capture the cell outline.

14. The method as claimed in claim 13, wherein the Sobel operator uses two 5×5 kernels to detect the cell outline of the cell image.

15. The method as claimed in claim 6, wherein the outline pixels are spaced on the cell outline.

16. The method as claimed in claim 6, wherein the tangents are identified using an artificial neural network (ANN) included in the image analyzing device.

17. The method as claimed in claim 6, wherein the image analyzing device calculates one of the brightness average and the hue average of the pixels on plural lines, wherein each of the lines is perpendicular to a specific one of the tangents and passes through a specific one of the outline pixels.

18. A method implemented by an image analyzing device for detecting whether a cell having a cell image is infected with a virus, comprising: (a) using the image analyzing device to capture a cell outline from the cell image, wherein the cell outline includes an outline pixel; (b) using the image analyzing device to identify a tangent of the outline pixel and define in relation to the tangent a first side and a second side opposite to the first side, wherein the first side indicates an extracellular region of the cell, and the second side indicates an intracellular region of the cell; (c) using the image analyzing device to calculate an optical parameter average of a plurality of pixels on both of the first side and the second side; and (d) using the image analyzing device to determine whether the cell is infected with the virus based on whether the optical parameter average on the first side is smaller than that on the second side.

19. The method as claimed in claim 18, wherein the optical parameter average comprises at least one of a brightness average and a hue average.

20. The method as claimed in claim 19, wherein the image analyzing device determines that the cell is infected with the virus when one of two states that the brightness average of the first side is smaller than that of the second side and the hue average of the first side is greater than that of the second side is true, and determines that the cell is not infected with the virus when one of the two states that the brightness average of the first side is greater than that of the second side and the hue average of the first side is smaller than that of the second side is true.

\* \* \* \* \*